(12) United States Patent
Booth et al.

(10) Patent No.: US 11,554,211 B2
(45) Date of Patent: Jan. 17, 2023

(54) CONNECTOR FOR ASEPTIC TRANSFER OF FLUID

(71) Applicant: Becton, Dickinson and Company, Franklin Lakes, NJ (US)

(72) Inventors: David E. Booth, West Milford, NJ (US); Gwenn Le Dimet, Charavines (FR); Peter Quinn, Ridgewood, NJ (US); Michael Vincent Quinn, East Hanover, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1105 days.

(21) Appl. No.: 16/160,081

(22) Filed: Oct. 15, 2018

(65) Prior Publication Data

US 2019/0111204 A1    Apr. 18, 2019

Related U.S. Application Data

(60) Provisional application No. 62/572,730, filed on Oct. 16, 2017.

(51) Int. Cl.
*A61M 5/145* (2006.01)
*A61M 39/18* (2006.01)
(Continued)

(52) U.S. Cl.
CPC ............ *A61M 5/145* (2013.01); *A61M 5/162* (2013.01); *A61M 5/2466* (2013.01); *A61M 39/14* (2013.01); *A61M 39/18* (2013.01); *A61M 5/158* (2013.01); *A61M 5/345* (2013.01); *A61M 39/162* (2013.01); *A61M 2005/247* (2013.01);
(Continued)

(58) Field of Classification Search
CPC .............. A61M 5/2466; A61M 5/2455; A61M 2005/247; A61M 2005/2474; A61M 2005/312; A61M 39/18
See application file for complete search history.

(56) References Cited

U.S. PATENT DOCUMENTS 4,019,512 A * 4/1977 Tenczar ................ A61M 39/14
604/905
6,679,529 B2 * 1/2004 Johnson .................. F16L 29/00
604/905

(Continued)

FOREIGN PATENT DOCUMENTS

CN       102971027 A       3/2013
CN       106489049 A       3/2017
(Continued)

*Primary Examiner* — Jenna Zhang
(74) *Attorney, Agent, or Firm* — The Webb Law Firm

(57) ABSTRACT

A drug delivery system for injecting a medicament may include a housing defining a cavity, a container received within the cavity and configured to receive a medicament with the container including a closure, a valve assembly received within the cavity and including a piercing member configured to pierce the closure of the container, and a connector arrangement provided between the container and the valve assembly, the connector arrangement movable between a first, pre-use position maintaining sterility between the closure of the container and the valve assembly and a second, use position permitting fluid communication between the container and the valve assembly.

5 Claims, 10 Drawing Sheets

(51) Int. Cl.
  *A61M 5/162*   (2006.01)
  *A61M 5/24*    (2006.01)
  *A61M 39/14*   (2006.01)
  *A61M 39/16*       (2006.01)
  *A61M 5/158*       (2006.01)
  *A61M 39/00*       (2006.01)
  *A61M 5/34*        (2006.01)
  *A61M 5/31*        (2006.01)

(52) U.S. Cl.
  CPC ............... *A61M 2005/312* (2013.01); *A61M 2039/0081* (2013.01)

(56) References Cited

U.S. PATENT DOCUMENTS

| | | |
|---|---|---|
| 8,998,858 B2 | 4/2015 | Chong et al. |
| 9,463,280 B2 | 10/2016 | Cabiri |
| 9,707,335 B2 | 7/2017 | Agard et al. |
| 9,707,337 B2 | 7/2017 | O'Connor et al. |
| 9,737,655 B2 | 8/2017 | Clemente et al. |
| 9,802,030 B2 | 10/2017 | Clemente et al. |
| 9,814,832 B2 | 11/2017 | Agard et al. |
| 9,999,727 B2 | 6/2018 | O'Connor et al. |
| 2002/0093192 A1* | 7/2002 | Matkovich ............... F16L 37/38 285/915 |
| 2003/0030272 A1 | 2/2003 | Johnson et al. |
| 2010/0022953 A1 | 1/2010 | Bochenko et al. |
| 2013/0110049 A1 | 5/2013 | Cronenberg et al. |
| 2013/0226143 A1 | 8/2013 | Davies et al. |
| 2014/0018742 A1* | 1/2014 | Sodhi .................... A61M 5/178 604/199 |
| 2015/0344161 A1 | 12/2015 | Selker et al. |
| 2017/0028132 A1* | 2/2017 | Cronenberg ........ A61M 5/2466 |

FOREIGN PATENT DOCUMENTS

| | | |
|---|---|---|
| EP | 3045189 A1 | 7/2016 |
| EP | 3061479 A1 | 8/2016 |
| JP | 2002514941 A | 5/2002 |
| JP | 2013542792 A | 11/2013 |
| JP | 2015526158 A | 9/2015 |
| WO | 2013155153 A1 | 10/2013 |
| WO | 2014179774 A1 | 11/2014 |
| WO | 2015081337 A2 | 6/2015 |
| WO | 2016141082 A1 | 9/2016 |
| WO | 2017089286 A1 | 6/2017 |
| WO | 2017177094 A2 | 10/2017 |

* cited by examiner

CONNECTOR FOR ASEPTIC TRANSFER OF FLUID

CROSS-REFERENCE TO RELATED APPLICATION

The present application claims priority to U.S. Provisional Application Ser. No. 62/572,730 filed Oct. 16, 2017, entitled "Connector for Aseptic Transfer of Fluid", the entire disclosure of which is hereby incorporated by reference.

BACKGROUND OF THE INVENTION

Field of the Invention

The present disclosure relates generally to a drug delivery device and, in particular, to a connector arrangement for aseptic transfer of fluid within the drug delivery device.

Description of Related Art

Various types of automatic injection or drug delivery devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

In one aspect, a drug delivery system for injecting a medicament includes a housing defining a cavity, a container received within the cavity and configured to receive a medicament with the container including a closure, a valve assembly received within the cavity and including a piercing configured to pierce the closure of the container, and a connector arrangement provided between the container and the valve assembly, the connector arrangement movable between a first, pre-use position maintaining sterility between the closure of the container and the valve assembly and a second, use position permitting fluid communication between the container and the valve assembly.

In another aspect, the connector arrangement may include at least one membrane held between the container and the valve assembly. The connector arrangement may include two membranes held between the container and the valve assembly. The at least membrane may include flashspun high-density polyethylene fibers. At least a portion of the connector arrangement may extend through and outside of the housing. The connector arrangement may be pulled out of the housing to move the connector arrangement from the first position to the second position.

In another aspect, a fluid transfer system utilizing a connector arrangement for aseptic transfer of fluid between a cannula arrangement and a container includes the cannula arrangement, the container, at least one membrane held between the cannula arrangement and the container, and at least one clip configured to clamp the at least one membrane between the cannula arrangement and the container.

In another aspect, the at least one membrane may include two membranes. The at least one clip may include two clips. The cannula arrangement may include a flange extending around a portion thereof. The container may include a flange extending around a portion thereof. The at least one clip may be configured to engage the flanges on the cannula arrangement and the container to clamp the at least one membrane between the cannula arrangement and the container. The cannula arrangement may include a housing and a cannula slidably positioned within the housing. The at least one membrane may include one of the following: a foil, rubber, or polymer. The at least one membrane may be pulled out of the housing to establish fluid communication between the cannula arrangement and the container. The container may include a syringe barrel. A joint member may be provided on a proximal end of the cannula arrangement and a joint member may be provided on a distal end of the container. The joint members may be configured to engage one another after the at least one membrane has been removed from between the cannula arrangement and the container. At least a portion of the at least one membrane may extend through the at least one clip.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION

Figure 1:
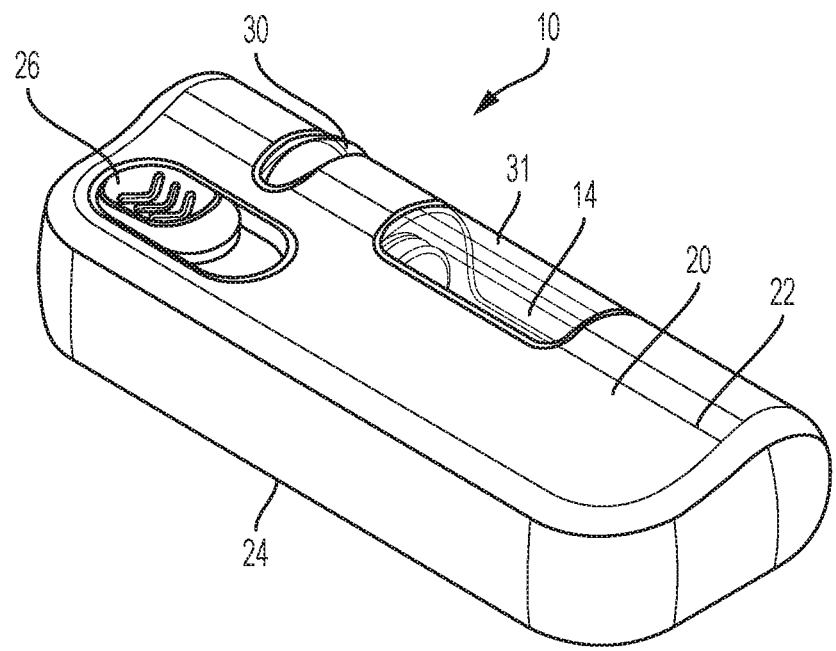
FIG. 1 is a perspective view of a drug delivery system according to one aspect of the present invention.
Figure 2:
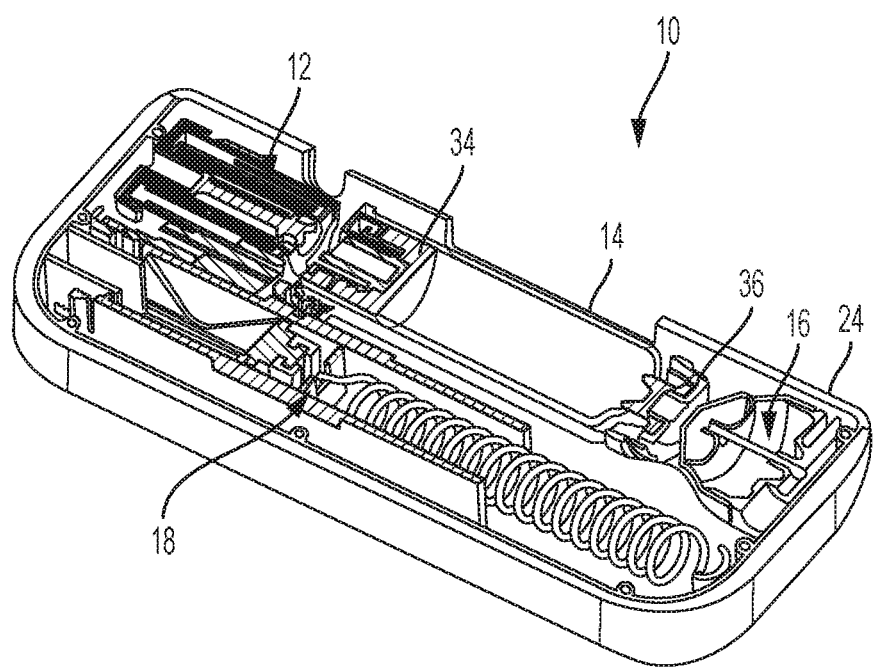
FIG. 2 is a perspective, cross-sectional view of the drug delivery system of FIG. 1 according to one aspect of the present invention.
Figure 3:
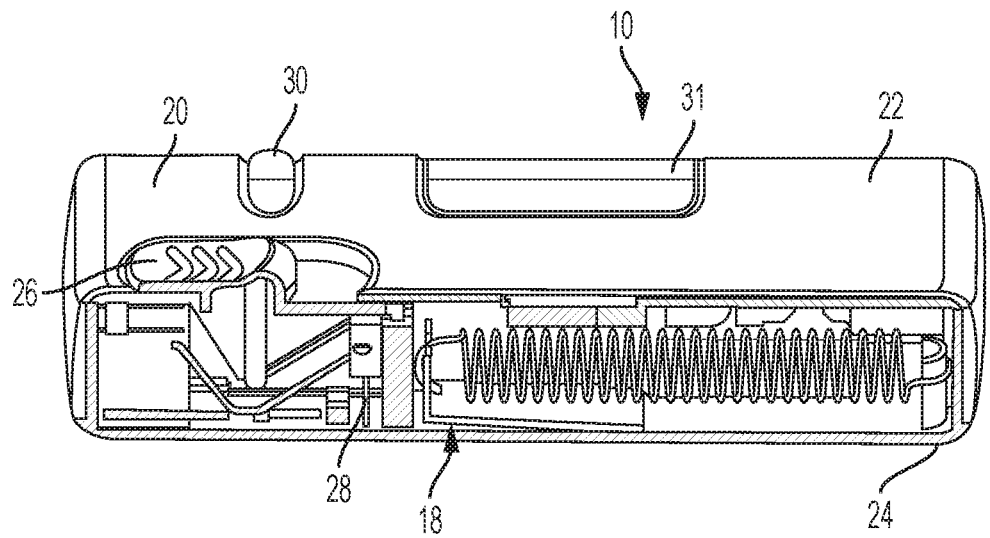
FIG. 3 is a front, cross-sectional view of the drug delivery system of FIG. 1 according to one aspect of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-15, a drug delivery system 10 according to one aspect of the present disclosure includes a drive assembly 12, a container 14, a valve assembly 16, and a needle actuator assembly 18. The drive assembly 12, the container 14, the valve assembly 16, and the needle actuator assembly 18 are at least partially positioned within a cavity defined by a housing 20. The housing 20 includes a top portion 22 and a bottom portion 24, although other suitable arrangements for the housing 20 may be utilized. In one aspect, the drug delivery system 10 is an injector device configured to be worn or secured to a user and to deliver a predetermined dose of a medicament provided within the container 14 via injection into the user. The system 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The system 10 may deliver the medicament at a fixed pressure to the user with the rate being variable. The general operation of the system 10 is described below in reference to FIGS. 1-15.

Referring again to FIGS. 1-15, the system 10 is configured to operate through the engagement of an actuation button 26 by a user, which results in a needle 28 of the needle assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. The housing 20 of the system 10 includes an indicator window 30 for viewing an indicator arrangement 32 configured to provide an indication to a user on the status of the system 10 and a container window 31 for viewing the container 14. The indicator window 30 may be a magnifying lens for providing a clear view of the indicator arrangement 32. The indicator arrangement 32 moves along with the needle actuator assembly 18 during use of the system 10 to indicate a pre-use status, use status, and post-use status of the system 10. The indicator arrangement 32 provides visual indicia regarding the status, although other suitable indicia, such an auditory or tactile, may be provided as an alternative or additional indicia.

Figure 4:
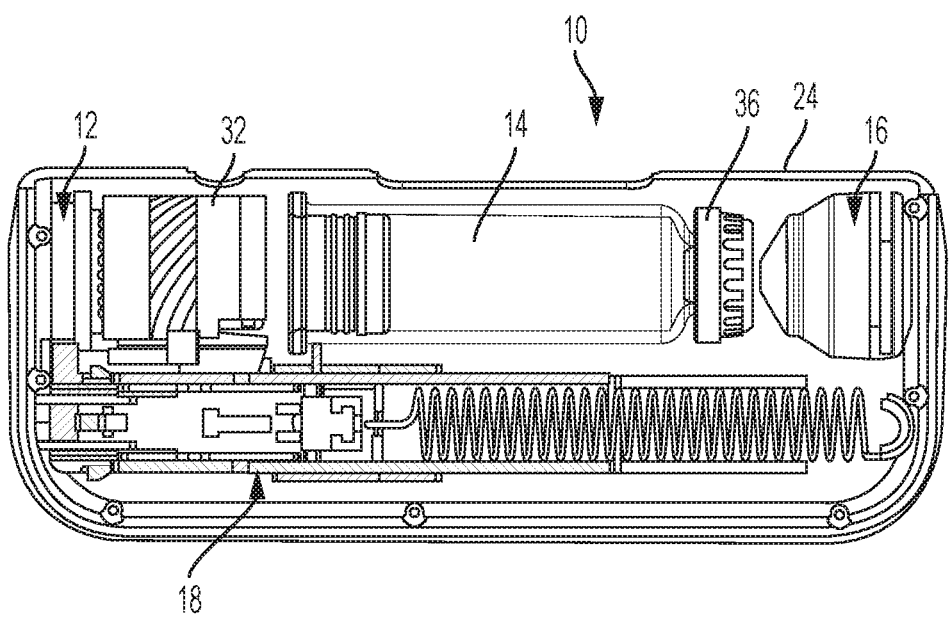
FIG. 4 is a top view of the drug delivery system of FIG. 1 according to one aspect of the present invention, showing a top portion of the housing removed and the drug delivery system in a pre-use position.
Figure 5:
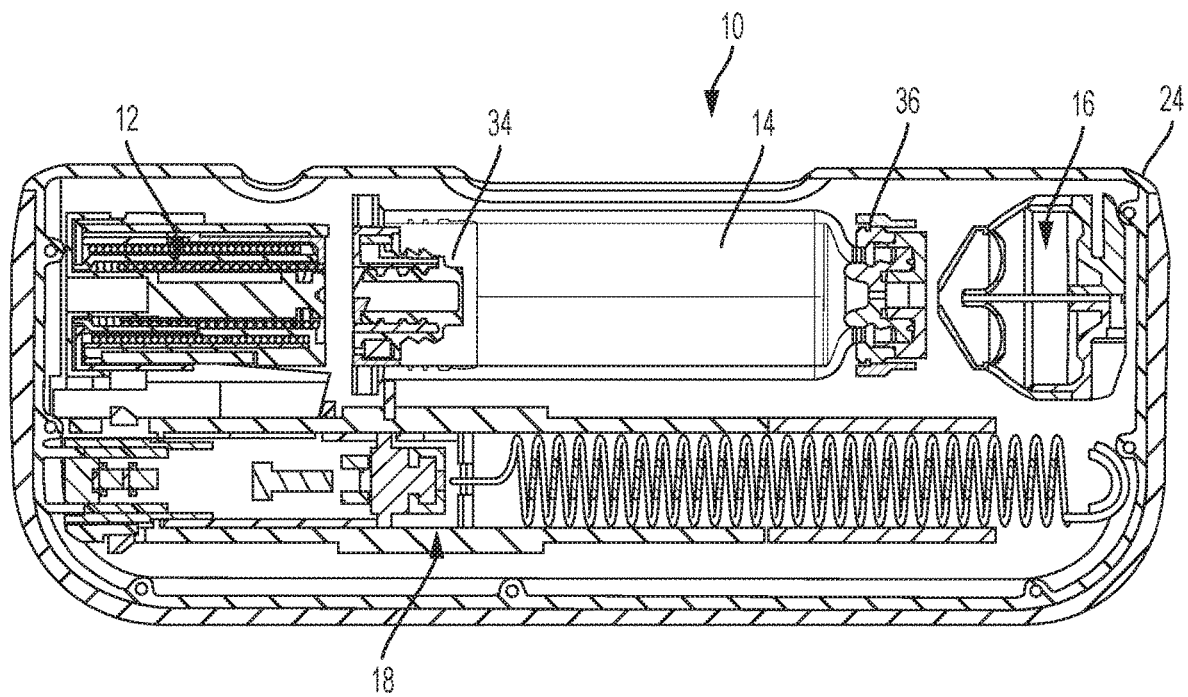
FIG. 5 is a top, cross-sectional view of the drug delivery system of FIG. 1 according to one aspect of the present invention, showing the drug delivery system in a pre-use position.
Figure 6:
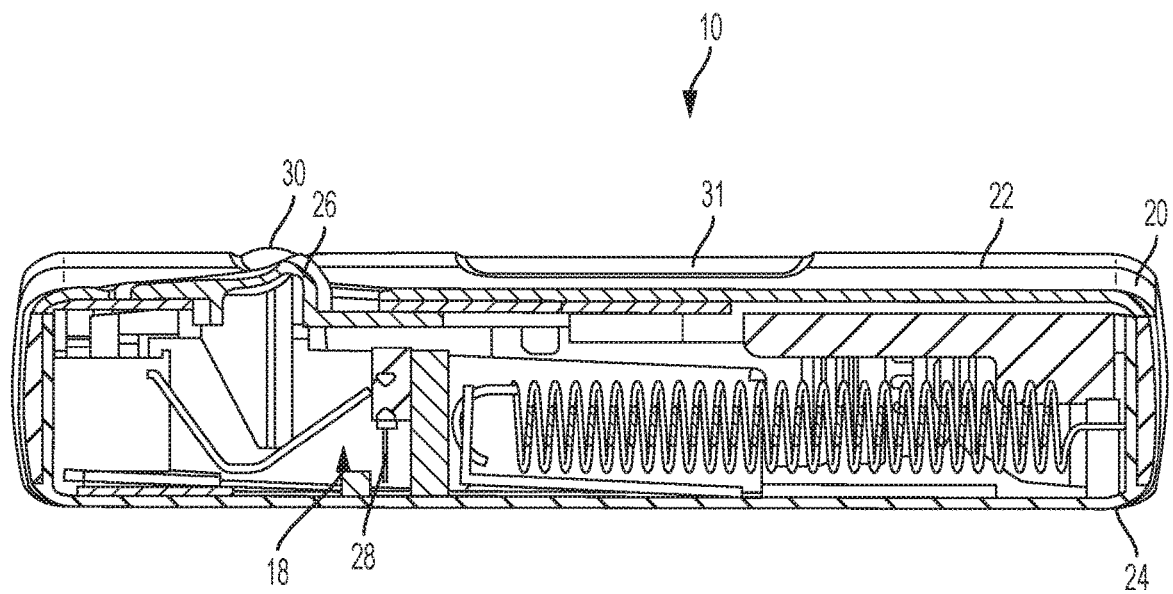
FIG. 6 is a front, cross-sectional view of the drug delivery system of FIG. 1 according to one aspect of the present invention, showing the drug delivery system in a pre-use position.
Figure 7:
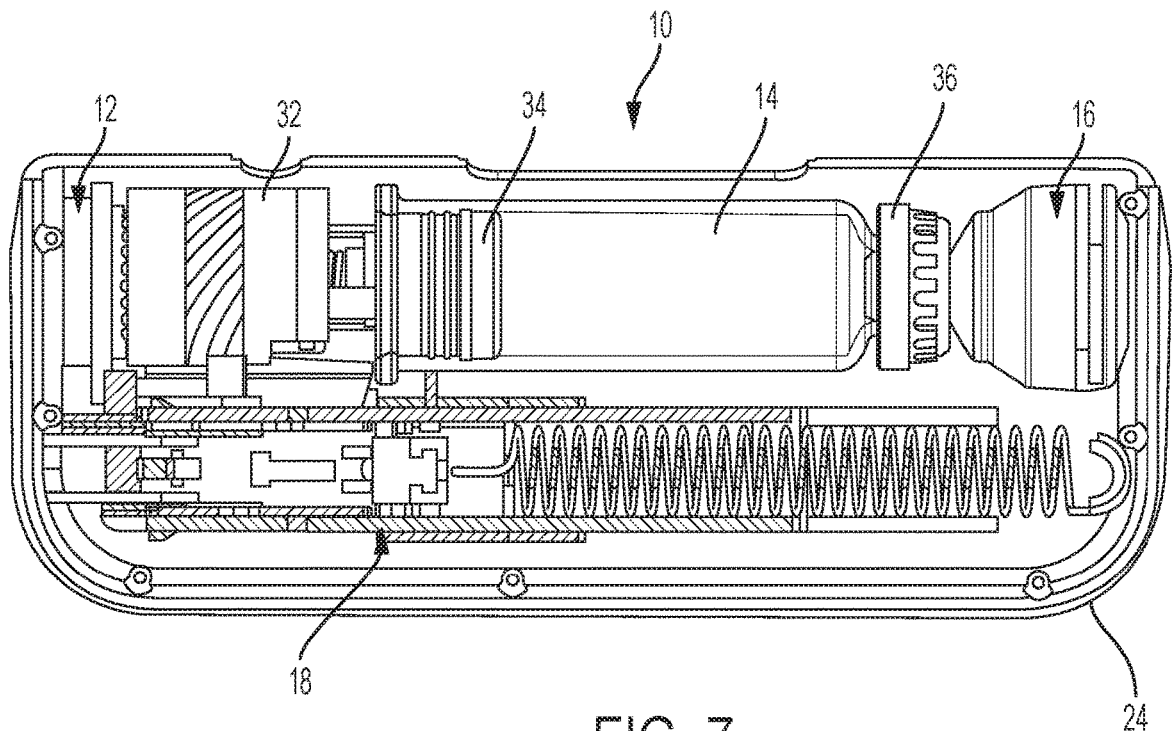
FIG. 7 is a top view of the drug delivery system of FIG. 1 according to one aspect of the present invention, showing a top portion of the housing removed and the drug delivery system in an initial actuation position.
Figure 8:
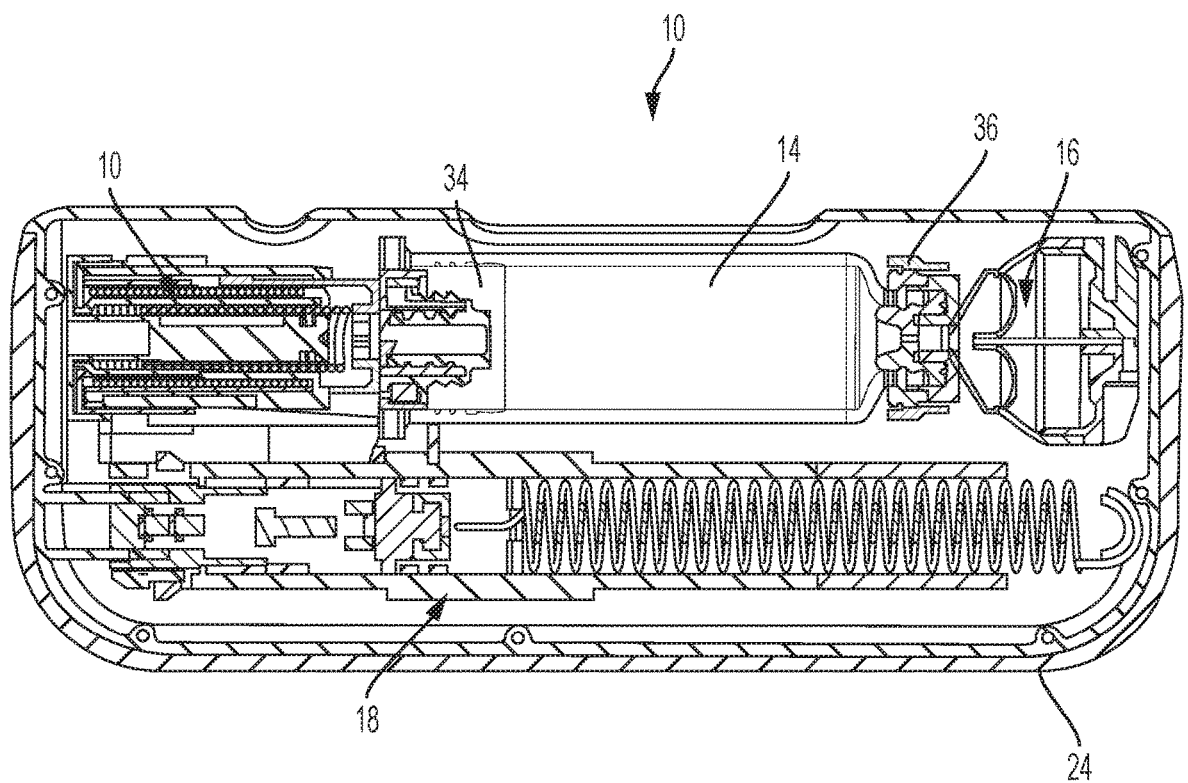
FIG. 8 is a top, cross-sectional view of the drug delivery system of FIG. 1 according to one aspect of the present invention, showing the drug delivery system in an initial actuation position.
Figure 9:
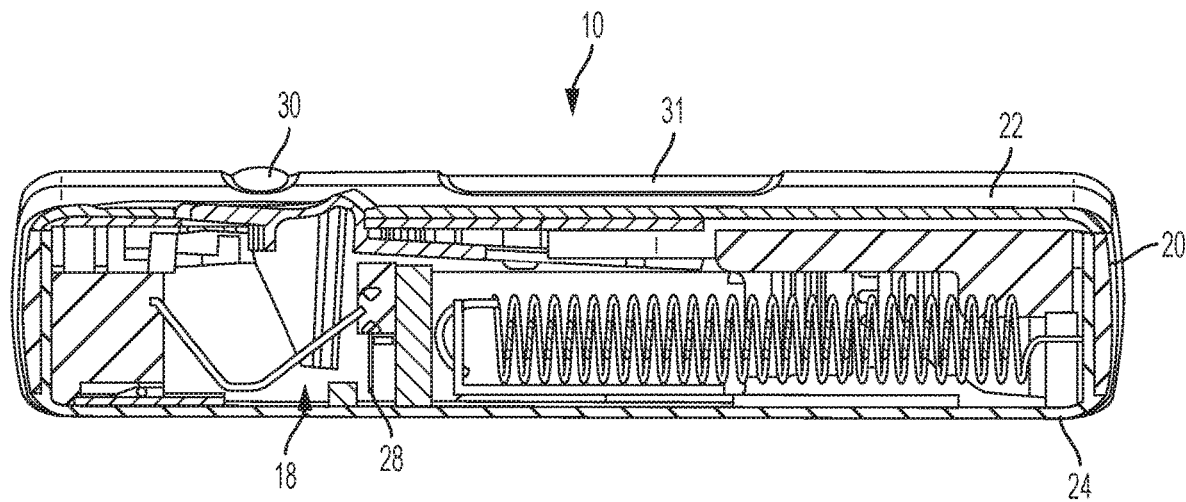
FIG. 9 is a front, cross-sectional view of the drug delivery system of FIG. 1 according to one aspect of the present invention, showing the drug delivery system in an initial actuation position.

Referring to FIGS. 4-6, during a pre-use position of the system 10, the container 14 is spaced from the drive assembly 12 and the valve assembly 16 and the needle 28 is in a retracted position. During the initial actuation of the system 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube (not shown) or other suitable arrangement. The drive assembly 12 is configured to engage a stopper 34 of the container 14, which will initially move the entire container 14 into engagement with the valve assembly 16 due to the incompressibility of the fluid or medicament within the container 14. The initial actuation of the system 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the system 10.

Figure 10:
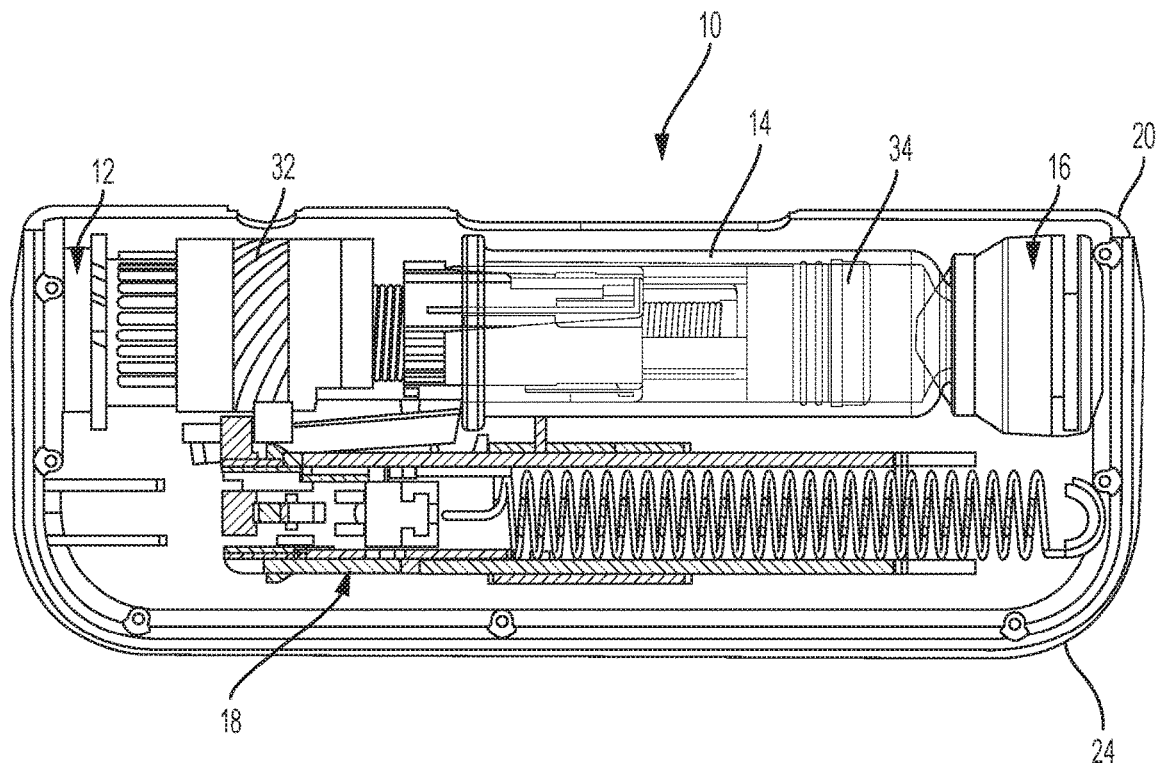
FIG. 10 is a top view of the drug delivery system of FIG. 1 according to one aspect of the present invention, showing a top portion of the housing removed and the drug delivery system in a use position.
Figure 11:
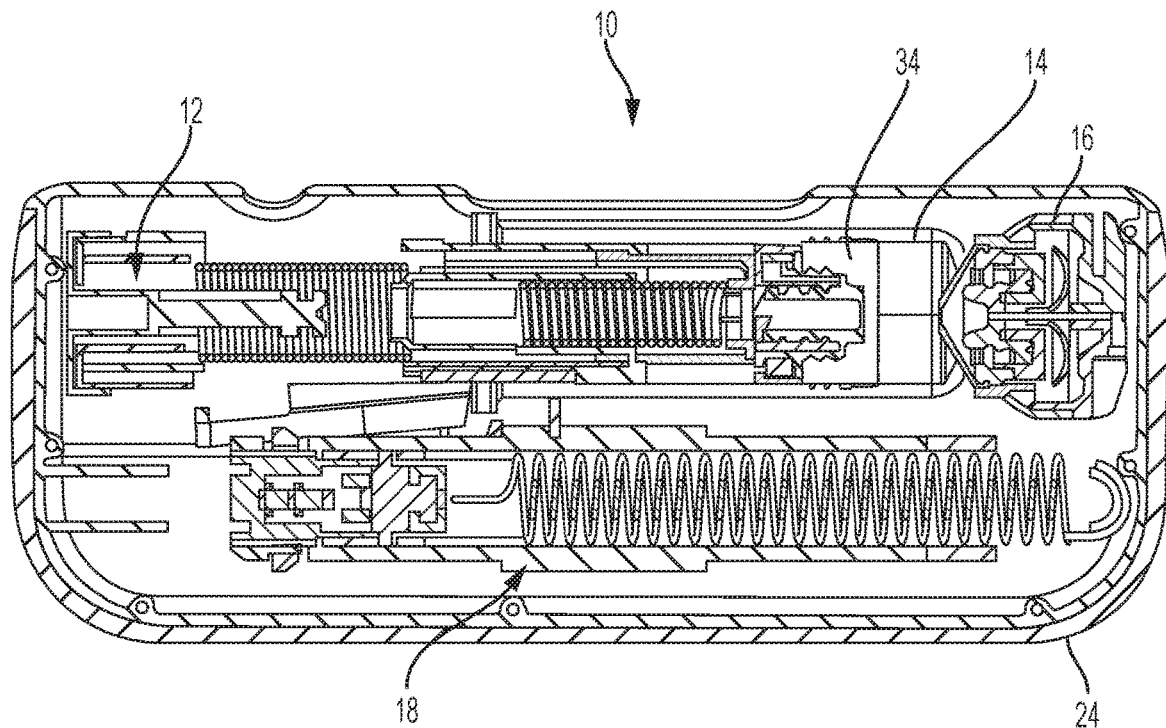
FIG. 11 is a top, cross-sectional view of the drug delivery system of FIG. 1 according to one aspect of the present invention, showing the drug delivery system in a use position.
Figure 12:
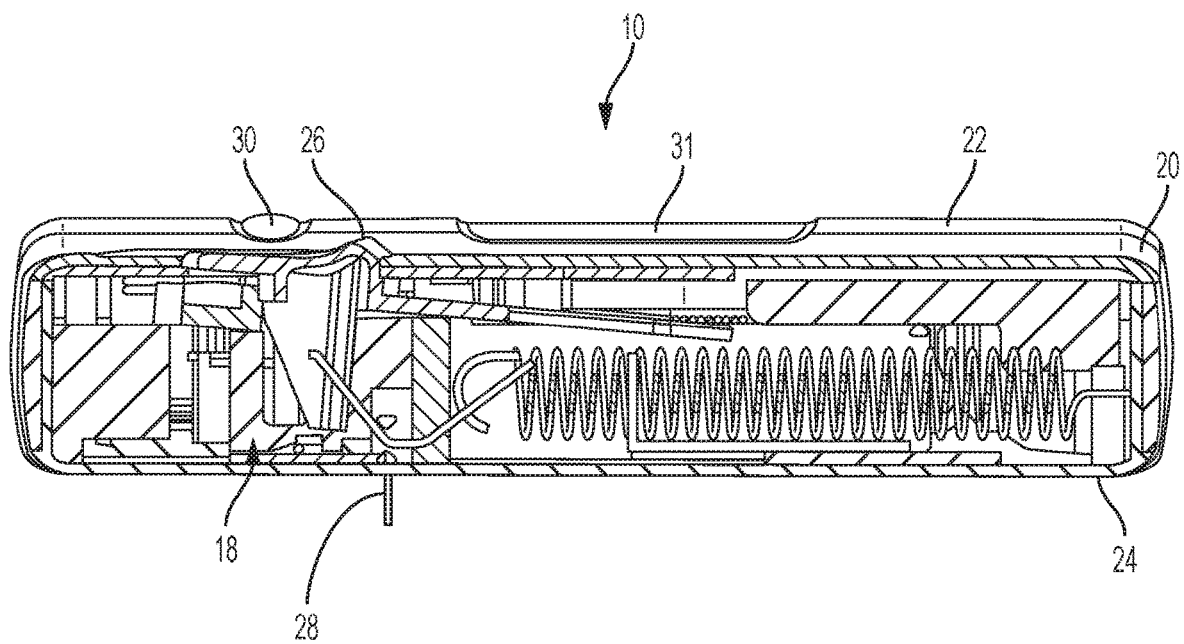
FIG. 12 is a front, cross-sectional view of the drug delivery system of FIG. 1 according to one aspect of the present invention, showing the drug delivery system in a use position.
Figure 13:
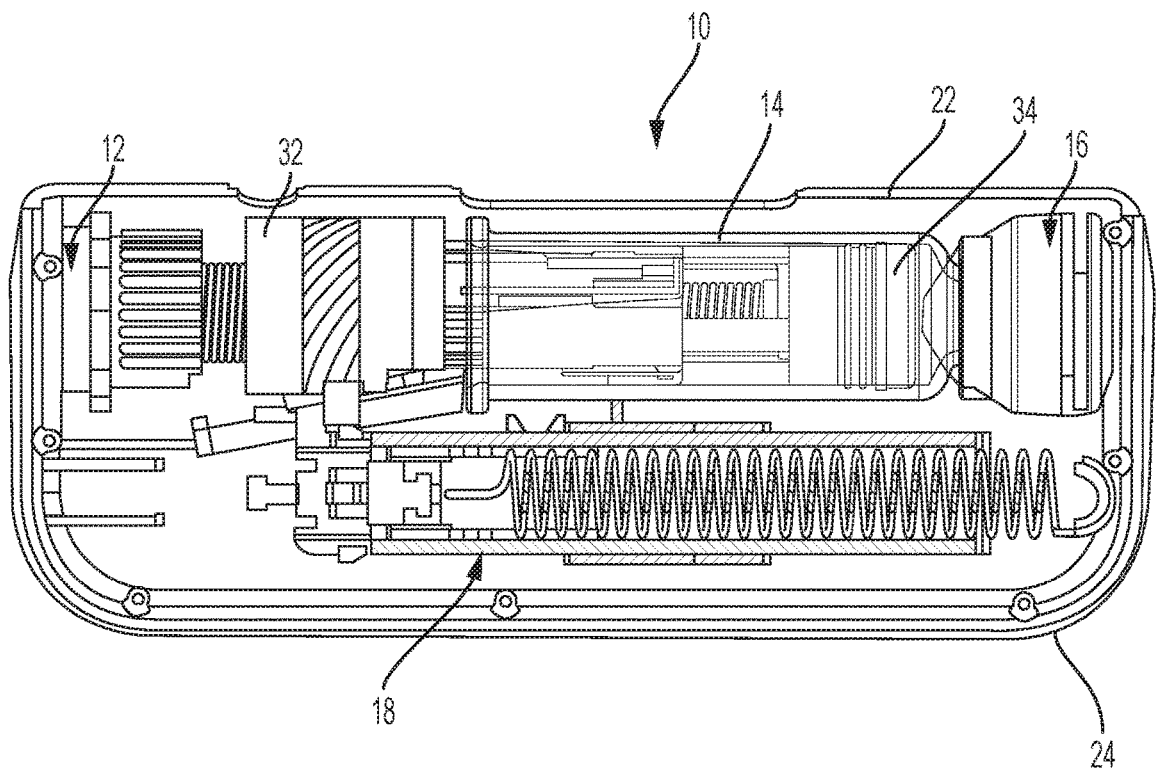
FIG. 13 is a top view of the drug delivery system of FIG. 1 according to one aspect of the present invention, showing a top portion of the housing removed and the drug delivery system in a post-use position.
Figure 14:
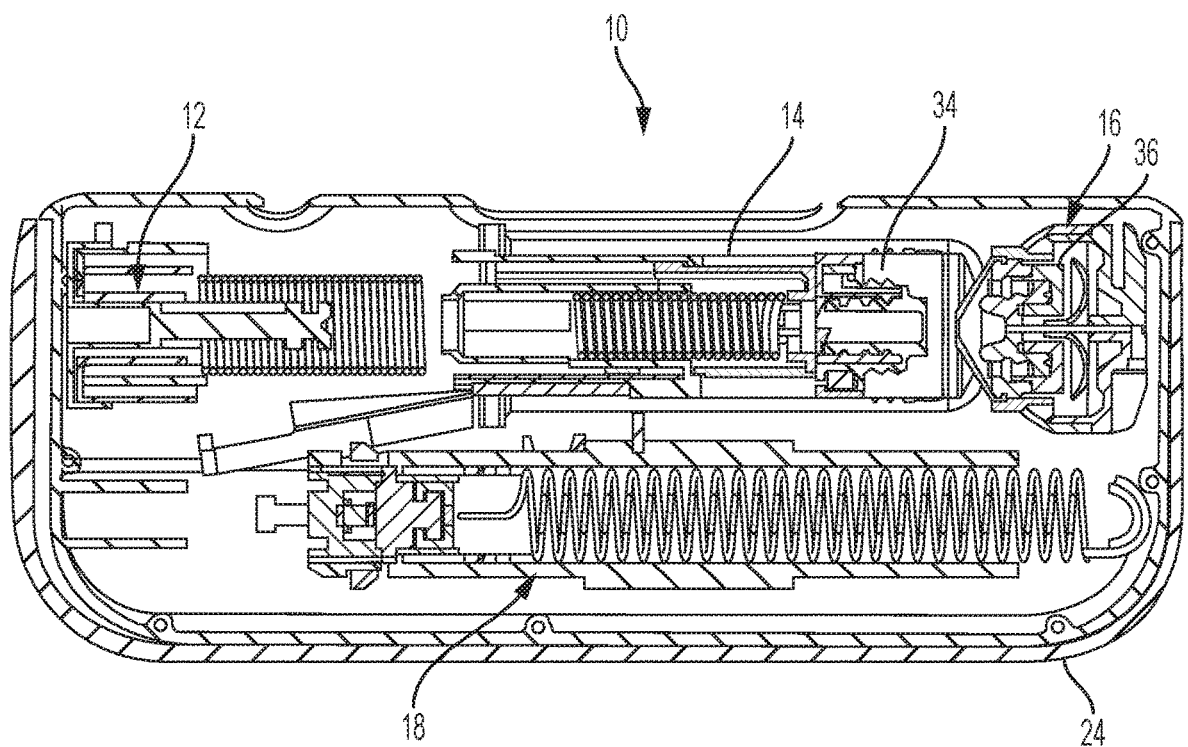
FIG. 14 is a top, cross-sectional view of the drug delivery system of FIG. 1 according to one aspect of the present invention, showing the drug delivery system in a post-use position.
Figure 15:
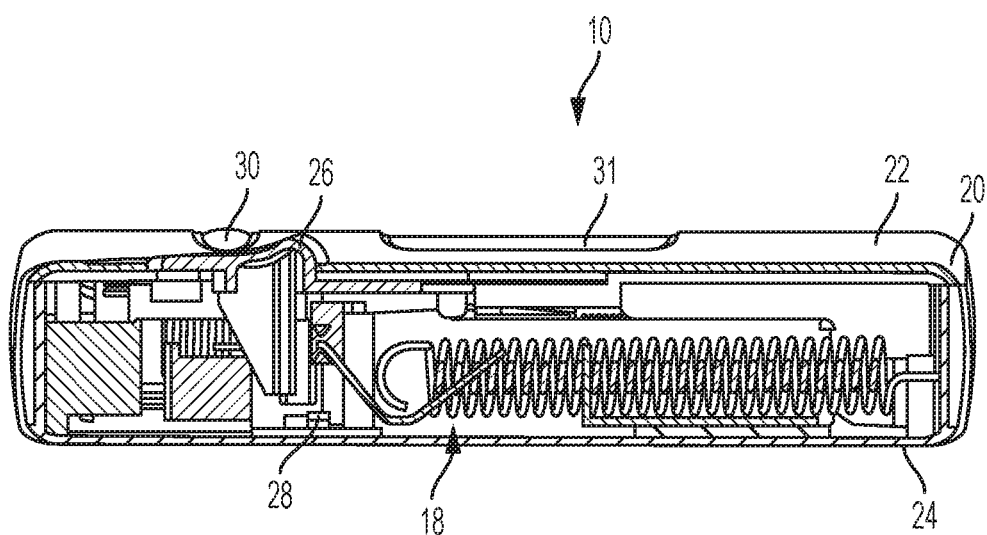
FIG. 15 is a front, cross-sectional view of the drug delivery system of FIG. 1 according to one aspect of the present invention, showing the drug delivery system in a post-use position.

During the use position of the system 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the system 10, shown in FIGS. 13-15, the needle 28 is in the retracted position and engaged with a pad 38 to seal the needle 28 and prevent any residual flow of fluid or medicament from the container 14. The container 14 and valve assembly 16 may be the container 14 and valve assembly 16 shown and described in International Publication No. WO 2015/081337, which is hereby incorporated by reference in its entirety.

Figure 16:
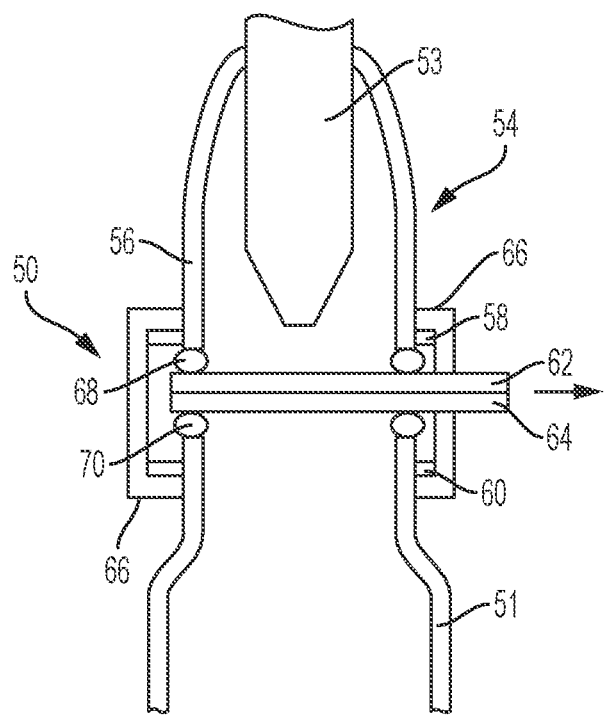
FIG. 16 is a side view of a connector for aseptic transfer of fluid in the drug delivery system of FIG. 1 according to one aspect of the present invention.
Figure 17A:
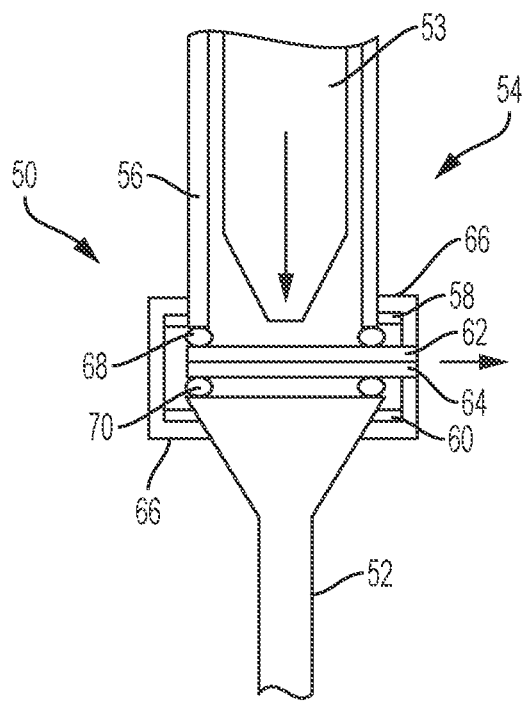
FIG. 17A is a side view of a connector for aseptic transfer of fluid in the drug delivery system of FIG. 1 according to another aspect of the present invention, the connector being shown in an inactive state.
Figure 17B:
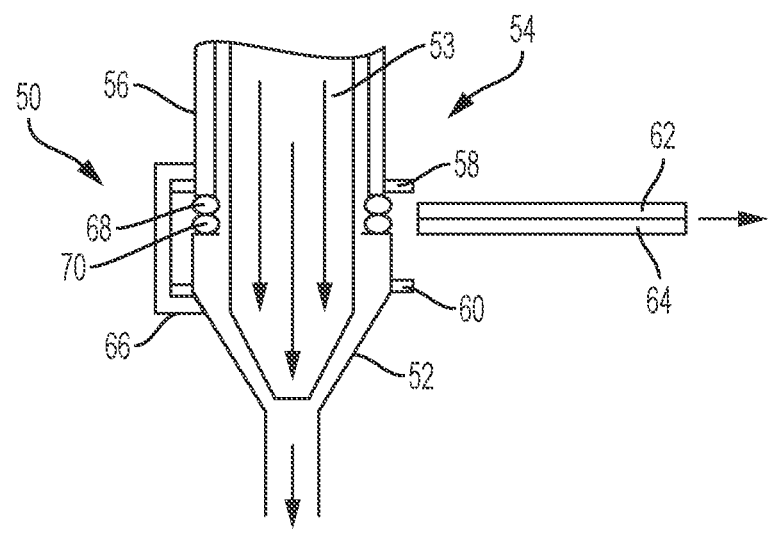
FIG. 17B is a side view of the connector of FIG. 17A, shown in an active state.

Referring to FIGS. 16-17B, in one aspect, a connector arrangement 50 is provided between two mating components to provide a sterile connection between the two components during fluid transfer. In one aspect, the connector arrangement 50 is provided between a syringe barrel or container 51, 52 and a cannula arrangement 54. The cannula arrangement 54 includes a cannula 53 surrounded by a housing 56 with a flange 58. The container 51, 52 also includes a corresponding flange 60. The container 51, 52 and the housing 56 each include a membrane 62, 64 to provide a sterile seal of the mating portions of the container 51, 52 and the housing 56. The membranes 62, 64 are made of any suitable material, such as a foil, rubber, or polymer, to maintain sterility of the container 51, 52, the cannula 53, and the housing 56 while allowing the membranes 62, 64 to be removed.

Referring again to FIGS. 16-17B, during assembly of the connector arrangement 50, a clip 66 or other similar type of connector is fitted to engage the respective flanges 58, 60 of the container 51, 52 and the housing 56 such that the membranes 62, 64 are brought into contact with one another. In one aspect, a single clip 66 is provided to clamp the flanges 58, 60 together with one another. In another aspect, two clips 66 are provided to clamp the flanges 58, 60 together with one another. The membranes 62, 64 may extend through one of the clips 66 once the connector arrangement 50 has been assembled. Prior to use of the cannula arrangement 54, the membranes 62, 64 are removed from the connector arrangement 50 to permit fluid communication between the container 51, 52 and the cannula 53. The membranes 62, 64 may be pulled away from the connector arrangement 50 to permit the container 51, 52 and the housing 56 to move into engagement with one another. In one aspect, a distal end of the container 51, 52 and a proximal end of the housing 56 may include joints 68, 70 to facilitate engagement between the container 51, 52 and the housing 56. The joints 68, 70 may be any type of engagement and locking mechanism that connects the distal end of the container 51, 52 with the proximal end of the housing 56.

Figure 18:
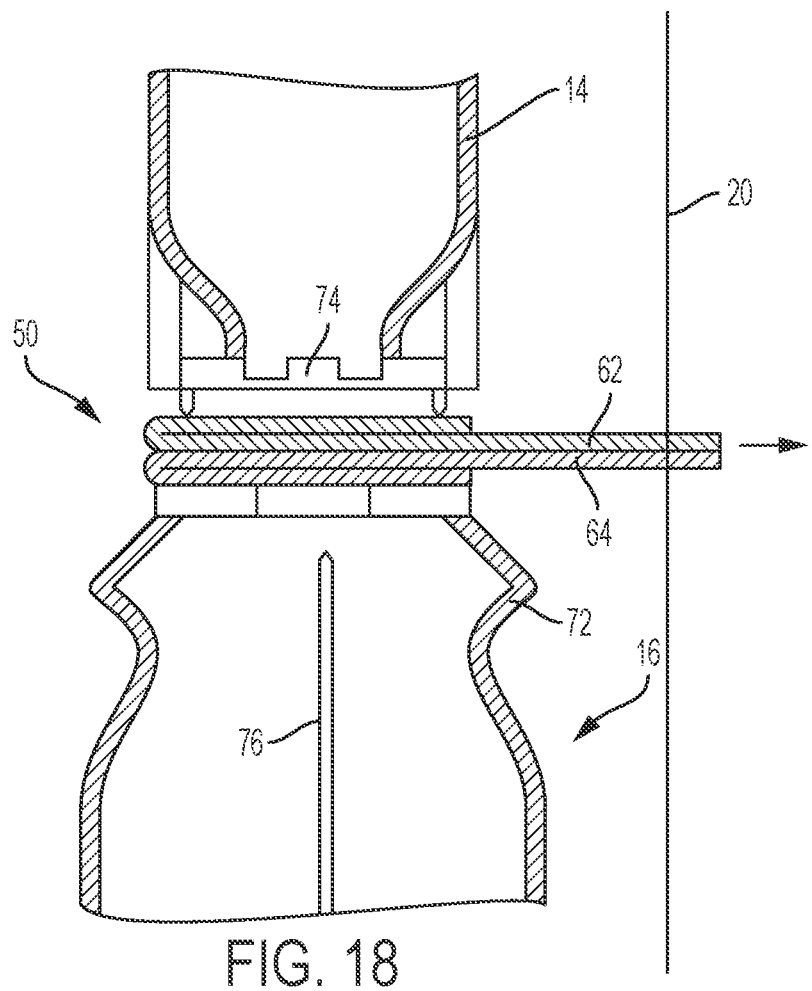
FIG. 18 is a side view of a connector for aseptic transfer of fluid in the drug delivery system of FIG. 1 according to another aspect of the present invention.

Referring to FIG. 18, the connector arrangement 50 is shown in use with the drug delivery system 10 shown in FIG. 1-15. The connector arrangement 50 is provided between the container 14 and the valve assembly 16. In particular, the membranes 62, 64 are held between a distal end of the container 14 and a proximal end of a valve member 72 of the valve assembly 16. In this aspect, the membranes 62, 64 form a pull tab that extends through and outside of the housing 20 of the system 10. The valve assembly 16 is configured to pierce a septum 74 held in the closure 36 of the container 14. During the drug delivery process of the system 10, the container 14 is pressed against the valve member 72 to expose a piercing member 76 housed in the valve member 72. The piercing member 76 pierces the septum 74 of the container 14 to establish fluid communication between the container 14 and the valve assembly 16. Prior to use of the system 10, however, the membranes 62, 64 are positioned between the container 14 and the valve assembly 16 to maintain the sterility of the components before use of the system 10. A portion of the membranes 62, 64 may extend out of the housing 20 of the system 10 to allow a user to grasp the membranes 62, 64. Before use of the system 10, the membranes 62, 64 are pulled from the housing 20 to allow the container 14 and the valve assembly 16 to move towards one another during the drug delivery process of the system 10. In this aspect, the membranes 62, 64 are made of flashspun high-density polyethylene fibers to allow pulling of the membranes 62, 64 without breaking or tearing the membranes 62, 64. It is contemplated, however, that other suitable materials may also be used for the membranes 62, 64.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drug delivery system for injecting a medicament, the system comprising:
    a housing defining a cavity;
    a container received within the cavity and configured to receive a medicament, the container comprising a closure;
    a valve assembly received within the cavity and comprising a piercing member configured to pierce the closure of the container; and
    a connector arrangement provided between the container and the valve assembly, the connector arrangement movable between a first, pre-use position in which the valve assembly is spaced apart from the container thereby maintaining sterility between the closure of the container and the valve assembly and a second, use position in which the container is advanced within the housing such that the piercing member pierces the closure thereby permitting fluid communication between the container and the valve assembly, wherein the connector arrangement is pulled out of the housing to move the connector arrangement from the first position to the second position.

2. The drug delivery system as claimed in claim 1, wherein the connector arrangement comprises at least one membrane held between the container and the valve assembly.

3. The drug delivery system as claimed in claim 2, wherein the at least one membrane of the connector arrangement comprises two membranes held between the container and the valve assembly.

4. The drug delivery system as claimed in claim 2, wherein the at least one membrane comprises flashspun high-density polyethylene fibers.

5. The drug delivery system as claimed in claim 1, wherein at least a portion of the connector arrangement extends through and outside of the housing.

\* \* \* \* \*